United States Patent
Fedosovsky et al.

(10) Patent No.: US 10,067,096 B2
(45) Date of Patent: Sep. 4, 2018

(54) APPARATUS, SYSTEM AND METHOD FOR AUTOMATED NONDESTRUCTIVE INSPECTION OF METAL STRUCTURES

(71) Applicant: Diakont Advanced Technologies, Inc., San Diego, CA (US)

(72) Inventors: Mikhail Evgenievich Fedosovsky, Saint Petersburg (RU); Mikhail Vladimirovich Sokolov, Saint Petersburg (RU); Edward Petit de Mange, Carlsbad, CA (US)

(73) Assignee: Dakont Advanced Technologies, Inc., San Diego, CA (US)

( * ) Notice: Subject to any disclaimer, the term of this patent is extended or adjusted under 35 U.S.C. 154(b) by 0 days.

(21) Appl. No.: 15/255,916

(22) Filed: Sep. 2, 2016

(65) Prior Publication Data

US 2017/0248554 A1    Aug. 31, 2017

Related U.S. Application Data

(63) Continuation of application No. PCT/RU2016/000219, filed on Apr. 18, 2016.

(30) Foreign Application Priority Data

Feb. 26, 2016 (RU) ................... 2016106942

(51) Int. Cl.
*G01N 29/265* (2006.01)
*G01N 33/20* (2006.01)
(Continued)

(52) U.S. Cl.
CPC ......... *G01N 29/265* (2013.01); *G01N 27/82* (2013.01); *G01N 27/902* (2013.01); *G01N 33/20* (2013.01); *G01N 2291/0234* (2013.01)

(58) Field of Classification Search
CPC .................. G01N 29/265; G01N 27/82
(Continued)

(56) References Cited

U.S. PATENT DOCUMENTS 4,137,778 A * 2/1979 Primbsch ............ B08B 3/12
73/627
5,357,198 A * 10/1994 Ando ............... G01N 27/82
324/225
(Continued)

FOREIGN PATENT DOCUMENTS

CA    2633271 A1   6/2007
CN    101915564 A  12/2010
(Continued)

OTHER PUBLICATIONS

Menegaldo et al: "SIRUS: A mobile robot for Floating Production Storage and Offloading (FPSO) ship hull inspection"; Department of Mechanical and Materials Engineering, Military Institute of Engineering, Rio de Janeiro—RJ, Brazil; Department of Mechatronics, Polytechnic School, University of Sao Paulo, SP, Brazil (downloaded Sep. 25, 2009): pp. 27-32.

(Continued)

*Primary Examiner* — Lisa Caputo
*Assistant Examiner* — Tarun Sinha
(74) *Attorney, Agent, or Firm* — Fox Rothschild LLP

(57) ABSTRACT

The provided apparatus for automated nondestructive inspection of a metal structure having a surface comprises an ultrasonic nondestructive inspection unit, a nondestructive inspection unit based on magnetic flux leakage method, an eddy-current nondestructive inspection unit, a control unit connected to the ultrasonic nondestructive inspection unit, the nondestructive inspection unit based on the magnetic flux leakage method and the eddy-current nondestructive inspection unit for sending control signals to carry out (Continued)

inspection of the metal structure, and a navigation unit connected to the control unit, wherein the navigation unit determines a position of said apparatus relative to the metal structure, determines a state of the surface of the metal structure and sends signals into the control unit. The non-destructive inspection unit based on magnetic flux leakage method changes a magnetic field induction generated by this unit from a minimum value close to zero value to a predetermined maximum value.

13 Claims, 7 Drawing Sheets

(51) Int. Cl.
*G01N 27/90* (2006.01)
*G01N 27/82* (2006.01)

(58) Field of Classification Search
USPC .......................................................... 73/618
See application file for complete search history.

(56) References Cited

U.S. PATENT DOCUMENTS

| | | | |
|---|---|---|---|
| 5,461,313 A | | 10/1995 | Bohon et al. |
| 5,514,956 A | | 5/1996 | Maxfield et al. |
| 6,104,970 A | | 8/2000 | Schmidt, Jr. et al. |
| 2002/0056809 A1 | | 5/2002 | Frederick et al. |
| 2002/0186009 A1* | 12/2002 | Makino | F16C 19/386 324/207.22 |
| 2011/0234212 A1* | 9/2011 | Lepage | G01N 27/82 324/219 |
| 2013/0014598 A1 | | 1/2013 | Langley et al. |
| 2013/0162439 A1* | 6/2013 | Schumacher | G01F 15/068 340/691.6 |
| 2014/0107947 A1* | 4/2014 | Papadimitriou | G01M 5/0033 702/34 |
| 2014/0196969 A1 | | 7/2014 | Jaffarullah et al. |
| 2016/0299031 A1 | | 10/2016 | Walker et al. |

FOREIGN PATENT DOCUMENTS

| | | |
|---|---|---|
| EP | 2506003 | 10/2012 |
| GB | 2491978 | 12/2012 |
| JP | H102221858 A | 9/1990 |
| RU | 94042545 A1 | 9/1996 |
| RU | 2231783 C2 | 6/2004 |
| RU | 94714 U1 | 5/2010 |
| RU | 117568 U1 | 6/2012 |
| RU | 2012140360 | 3/2014 |
| RU | 139681 U1 | 4/2014 |
| RU | 142323 U1 | 6/2014 |
| RU | 2539777 C1 | 1/2015 |
| WO | 1998045728 | 10/1998 |
| WO | 2009156862 | 12/2009 |
| WO | 2011084143 A1 | 7/2011 |
| WO | 20160732244 A1 | 5/2016 |

OTHER PUBLICATIONS

Marsh et al: "Robotic Underwater Corrosion Inspection/Assessment of Sheet Pile Along Two Rivers at Cleveland, Ohio", US Army Corps of Engineers, Construction Engineering Research Laboratories, Technical Report 99/37 (May 1999); (92 pages).

Weber et al: "Development of the Neptune On-Stream Robotic Inspection System for Above-Ground Storage Tanks" US Army Corps of Engineers, Construction Engineering Research Laboratories, Technical Report 98/20 (Dec. 1997); (39 pages).

Sattar et al., "Amphibious NDT Robots, Climbing and Walking Robots: towards New Applications," Houxiang Zhang (Ed.) (2007), ISBN: 978-3-902613-16-5; pp. 127-151.

Page print: http://petrobotproject.eu/mec-technique-for-challenging-tank-floor-inspection/ (Sep. 1, 2106); pp. 1-4.

* cited by examiner

APPARATUS, SYSTEM AND METHOD FOR AUTOMATED NONDESTRUCTIVE INSPECTION OF METAL STRUCTURES

CROSS-REFERENCE TO RELATED APPLICATIONS

This application is a Continuation of International Application No. PCT/RU2016/000219, filed Apr. 18, 2016, which claims priority to Russian Patent Application No. 2016106942, filed Feb. 26, 2016. The disclosures of which are incorporated herein by reference.

BACKGROUND OF THE INVENTION

Field of the Invention

The present invention generally relates to apparatuses for automated nondestructive inspection (NDI) of metal structures, and, in particular, to apparatuses for automated nondestructive inspection of storage tanks for petroleum and petroleum products.

Prior Art

At present time different apparatuses for automated nondestructive inspection of metal structures are known, in particular, for inspection the bottoms of storage tanks for petroleum and petroleum products. Generally, apparatuses for nondestructive inspection based on the magnetic flux leakage method, which are used alone or in combination with apparatuses based on other non-destructive inspection methods are employed for nondestructive inspection. However all known apparatuses or systems for nondestructive inspection based on magnetic flux leakage method cannot provide inspection of various types of tank bottoms without direct human involvement, which often leads to the need for emptying and degassing of tanks.

For example, U.S. Pat. No. 5,514,956 discloses an apparatus for a storage tank bottom inspection based on a magnetic flux leakage method, which provides the possibility to decrease magnetic attraction of the apparatus device to the tank bottom in the presence of obstacles on the bottom surface by removing corresponding magnetic apparatus block from the surface of tank bottom. However, such decrease in magnetic attraction is to be provided by operator directly holding said apparatus and performing its movement, making it impossible to use said apparatus in the tank without emptying and degassing thereof. Furthermore, the use of other methods for nondestructive inspection in combination with the magnetic flux leakage method is not applicable in this apparatus, thus making the inspection by means of said apparatus less accurate.

Part of these disadvantages has been solved in the apparatus disclosed in U.S. Pat. No. 6,104,970, which is an automated apparatus for storage tank bottom inspection connected to remote station. Said apparatus can move along the surface of a tank bottom to be inspected, and comprises electromagnetic sensor and ultrasound sensors to enable nondestructive inspection of this bottom. Furthermore, the apparatus comprises a sensor to determine a butt or lap welded joint between the plates at the tank bottom, the signal from which enables removing of an electromagnetic sensor magnet to prevent a collision with the joint. However, in this case the inspection of tank bottom area at the location of joint and around it either is not performed, or a inspection accuracy of this area decreases significantly, thus decreasing greatly the overall inspection accuracy of entire bottom performed by means of said apparatus, especially in the presence of plurality of obstacles on the bottom to be inspected. Furthermore, the removing of the electromagnetic sensor magnet may not be a sufficient measure to allow for preventing collision with the butt or lap joint and magnetic attraction of magnet to the joint.

Thus, there is a vital need to provide an apparatus for nondestructive inspection, which can operate in the automatic or semi-automatic mode throughout the metal structure to be inspected comprising different obstacles and heterogeneities.

SUMMARY

The objective of the present Invention is to provide a device for automated nondestructive inspection of metal structures, which allows conducting an accurate inspection of different types of metal structures, including metal structures containing obstacles on their surfaces, for example, in a form of the butt or lap joints of plates constituting thereof, and which can also operate in the automatic or semi-automatic mode.

The proposed apparatus for automated nondestructive inspection of a metal surface comprises an ultrasonic nondestructive inspection unit, a nondestructive inspection unit based on magnetic flux leakage method, an eddy-current nondestructive inspection unit, a control unit connected to the ultrasonic nondestructive inspection unit, the nondestructive inspection unit based on magnetic flux leakage method, the eddy-current nondestructive inspection unit for sending control signals to carry out inspection of the metal structure, and a navigation unit connected to the control unit, wherein the navigation unit determines a position of said apparatus relative to the metal structure, determines a state of the surface of the metal structure and sends signals into the control unit with information about the position of said apparatus and the state of the surface of the metal structure to be inspected. All said units are installed in a housing, the housing comprising a means for moving said apparatus for automated nondestructive inspection over the surface of the metal structure to be inspected. The control unit sends the control signals simultaneously to at least one of the ultrasonic nondestructive inspection unit, the nondestructive inspection unit based on magnetic flux leakage method and the eddy-current nondestructive inspection unit based on the signals received from the navigation unit. The nondestructive inspection unit based on magnetic flux leakage method changes a magnetic field induction generated by this unit from a minimum value close to zero value to a predetermined maximum value.

The achieved technical result is that the proposed apparatus is capable of performing automated nondestructive inspection of metal structures having different types of metal surfaces, including metal surfaces of varying thickness. In addition, the combined use of different nondestructive inspection units allows performing more accurate and rapid inspections of metal structures without the need for multiple passages of the apparatus close to the same surface area of the metal structures to be inspected.

According to one of the embodiments, the apparatus further comprises at least one nondestructive inspection unit.

According to another embodiment, the apparatus further comprises a unit for cleaning the surface of the metal structure.

According to yet another embodiment, the nondestructive inspection unit based on magnetic flux leakage method is characterized by a working gap between this unit and the surface of the metal structure to be inspected and is configured to change said working gap.

According to yet another embodiment, the nondestructive inspection unit based on magnetic flux leakage method comprises a magnetic system comprising at least two magnetic drums connected by a flux guide frame, wherein said at least two magnetic drums are configured to rotate with respect to each other.

According to yet another embodiment, the apparatus further comprises a means of emergency removing said apparatus from the metal structure.

According to yet another embodiment, all said units are explosion-proof and/or are contained within sealed explosion-proof housings.

According to yet another embodiment, the navigation unit comprises at least one sound imager, at least one ultrasound sensor and/or at least one camera.

According to yet another embodiment, the apparatus is used to inspect storage tanks for petroleum, petroleum products, and petrochemicals.

According to yet another embodiment, the apparatus is used to inspect storage tanks for water.

Furthermore, also proposed is a system for automated nondestructive inspection of a metal structure, the system comprising: the apparatus for automated nondestructive inspection of a metal structure, and a control center designed for controlling the apparatus and connected to the apparatus via an explosion-proof communication line.

According to yet another embodiment, the inspection system comprises a vehicle-mounted laboratory.

Furthermore, also proposed is a method for nondestructive inspection of a metal structure by the apparatus, the method comprising: providing an access for said apparatus to the metal structure to be inspected, inspecting a part of the metal structure adjacent to said apparatus simultaneously using at least one of the ultrasonic nondestructive inspection unit, the nondestructive inspection unit based on magnetic flux leakage method and the eddy-current nondestructive inspection unit, and moving said apparatus over the surface of the metal structure to another part of the metal structure using information from the navigation unit of the apparatus. A magnetic field induction in the nondestructive inspection unit based on magnetic flux leakage method is changed at a change in parameters of the metal structure.

According to yet another embodiment, a working gap between the nondestructive inspection unit based on the magnetic flux leakage method and the surface of the metal structure to be inspected is changed in case of presence of obstacles on the metal structure surface.

According to yet another embodiment, the method further comprises cleaning of the metal structure surface in case of detection of depositions present on the metal structure surface.

Other aspects of the present invention may be understood from the following description of the preferred embodiments and the drawings.

DETAILED DESCRIPTION OF THE PREFERRED EMBODIMENTS

The present description discloses embodiments and distinctive features of an apparatus for automated nondestructive inspection (NDI) of metal structures, in particular, for inspection the bottoms of storage tanks for petroleum and petroleum products, also performed inside such tanks.

As used herein, the term "automated" refers both to an apparatus that operates fully automatically, and to an apparatus that operates automatically and at the same time acts with the participation of a user, i.e., to the apparatus that operates either in the automatic or semi-automatic mode.

Hereafter, some embodiments of the present invention are described in details. It should be noted that the special features of the disclosed apparatus for automated nondestructive inspection of metal structures disclosed in any embodiment may be inherent to the various embodiments in any combination thereof, until otherwise is specified.

Figure 1:
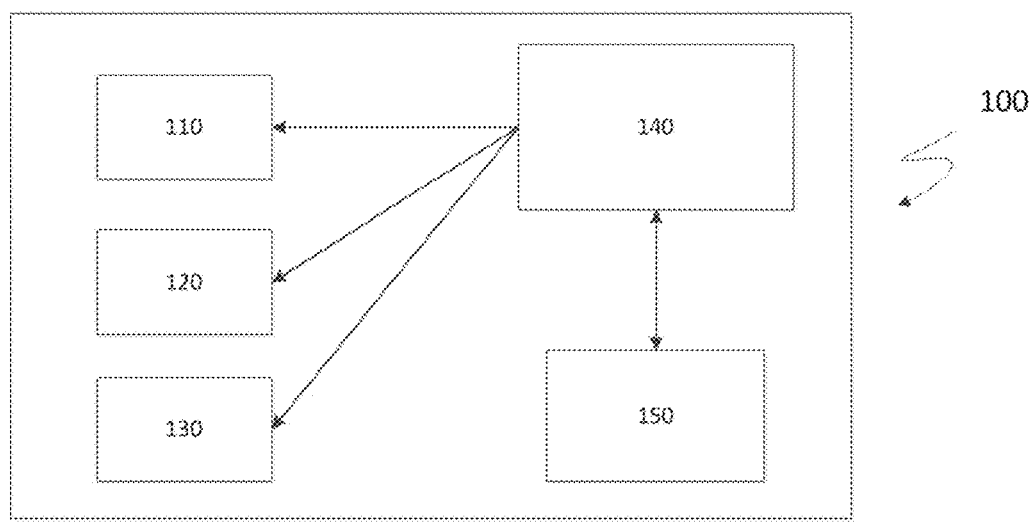
FIG. 1 shows a schematic diagram of an apparatus for automated nondestructive inspection of metallic structures according to the first embodiment.

FIG. 1 shows schematic diagram of the proposed apparatus 100 for automated nondestructive inspection of a metal structure according to the first embodiment. The apparatus 100 comprises three nondestructive inspection units, namely, ultrasound nondestructive inspection unit 110, unit 120 for nondestructive inspection based on magnetic flux leakage method (MFL (Magnetic Flux Leakage) unit) and eddy-current nondestructive inspection unit 130. Furthermore, the apparatus 100 comprises a control unit 140, which is connected to three specified nondestructive inspection units 110, 120 and 130 for sending control signals to provide inspection of the metal structure, and a navigation unit 150, connected to the control unit 140. MFL unit 120 has the functionality to change a working gap between the surface thereof and the surface of the metal structure to be inspected, which is needed, for example, when automated nondestructive inspection apparatus 100 moves over the obstacles on the metal structure surface.

The navigation unit 150 is intended to determine position of said apparatus 100 relative to the metal structure, as well as to evaluate a state of the surface of the metal structure to be inspected if necessary. Furthermore, the navigation unit 150 can send signals containing information about the position of said apparatus 100 and the state of the surface of the metal structure to be inspected to the control unit 40.

In turn, the control unit 140 is intended to send control signals simultaneously to, at least, one of said three units, nondestructive inspection units 110, 120 and 130 on the basis of signals, received from the navigation unit 150.

Important feature of the present invention is that MFL unit 120 is made such that a magnetic field induction, created by this unit, can be changed from a minimum value, such as close to zero, to a predetermined maximum value. Such a change can be done in the automatic or semi-automatic mode.

All the units constituting the above apparatus 100 are mounted in a housing, which is provided with the means for moving (not shown) said apparatus over the metal structure surface, for example, over the bottom surface of petroleum and petroleum product storage tank.

It should be noted that according to the other embodiments the apparatus for automated nondestructive inspection of a metal structure can have another set of nondestructive inspection units, for example, a greater number of them, or only one MFL unit. Furthermore, nondestructive inspection units based on the other methods for nondestructive inspection, known to those skilled in the art, can be used, for example, based on electric, radiation, thermal, radiofrequency, acoustic methods and others.

Figure 2A:
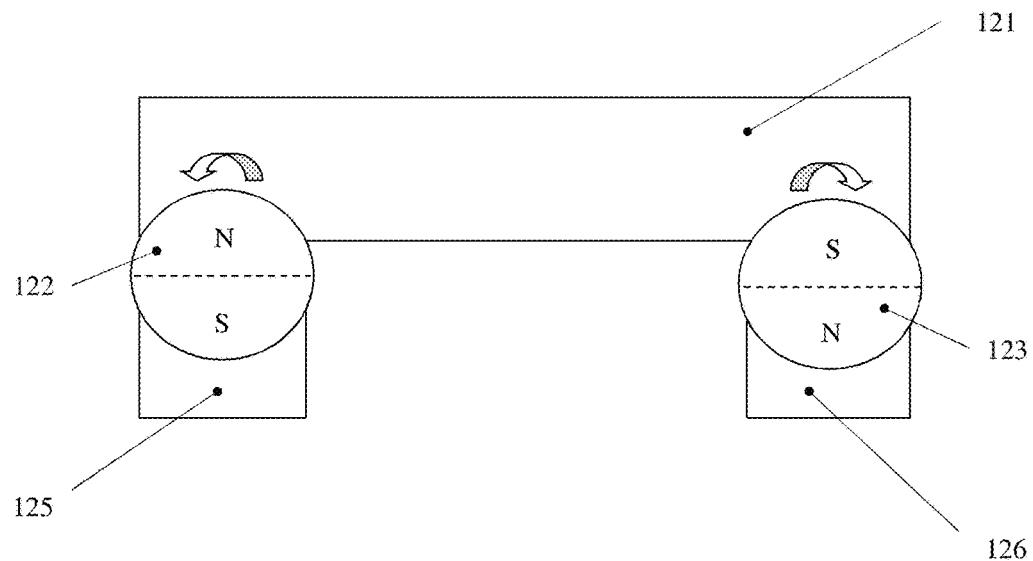
FIGS. 2A and 2B illustrate a magnetic system of a unit for nondestructive inspection based on magnetic flux leakage method in the SWITCHED-ON state (FIG. 2A) and in the SWITCHED-OFF state (FIG. 2B), accordingly.
Figure 2B:
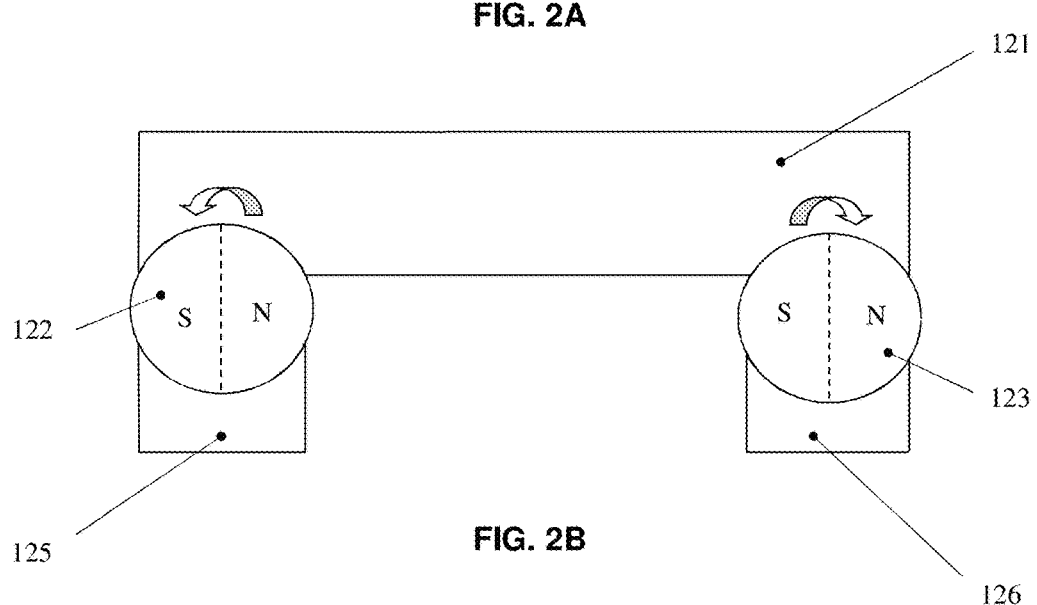

MFL unit 120 can be realized by any method known to those skilled in the art, so as to provide changeability of magnetic field induction, induced by this unit. For example, in the apparatus according to the first embodiment MFL unit 120 comprises a magnetic system, illustrated in FIG. 2A and 2B, comprising a flux guide frame 121, two magnetic drums 122, 123 and pole pieces 125, 126. The magnetic field is adjusted by rotating magnetic drums to predetermined angles. In FIG. 2A the magnetic system of MFL unit is in the switched-on state, characterized by a certain value of magnetic field induction that is greater than zero, and in FIG. 2B said magnetic system is set to a switched-off state wherein via rotation of magnetic drums the value of magnetic field induction is at the minimum value close to zero value, due to the presence of remnant magnetism. Thus, the magnetic system with an adjustable magnetic field in the MFL unit allows to optimize the value of the magnetic field, for specific thicknesses of the metal structure to be inspected, as well as to the clean MFL unit from the adhered magnetic dirt.

Due to these features of the magnetic system, the MFL unit can pass the metal structure in places where its parameters change, for example, in locations of the butt or lap joints of plates constituting the metal structure, or in presence of the obstacles in a form of contaminations, residue, deposits or the like.

Figure 3:
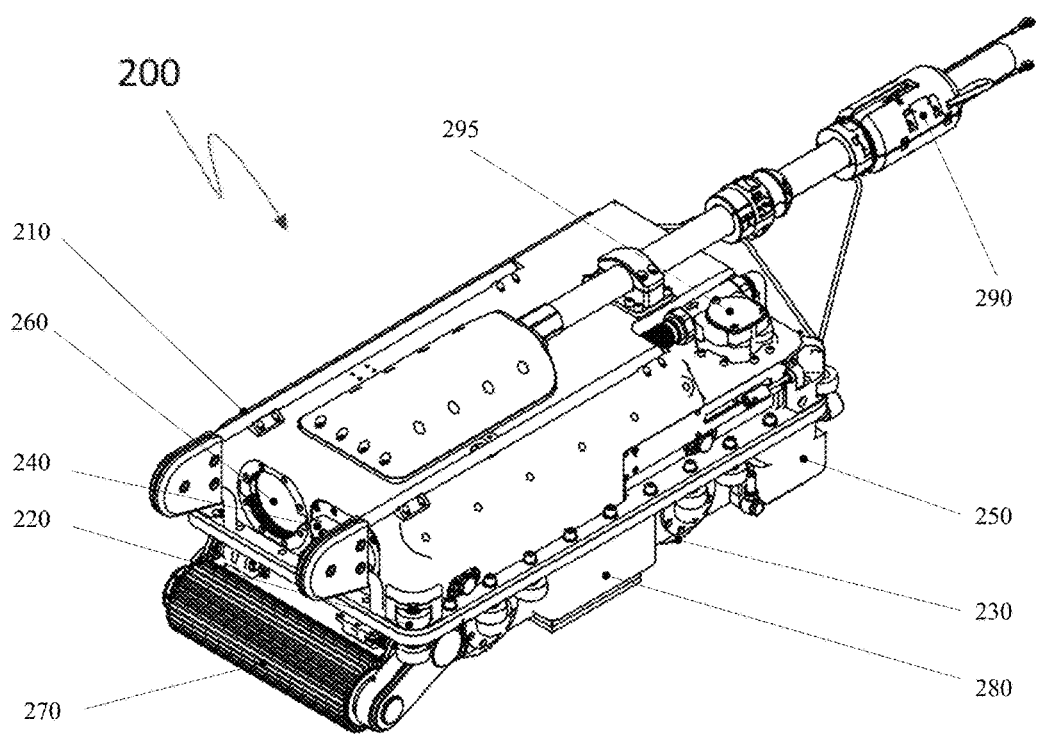
FIG. 3 shows a three-dimensional view of the apparatus for automated nondestructive inspection of a metal structure according to the second embodiment, providing visibility of the upper portion of said apparatus.
Figure 4:
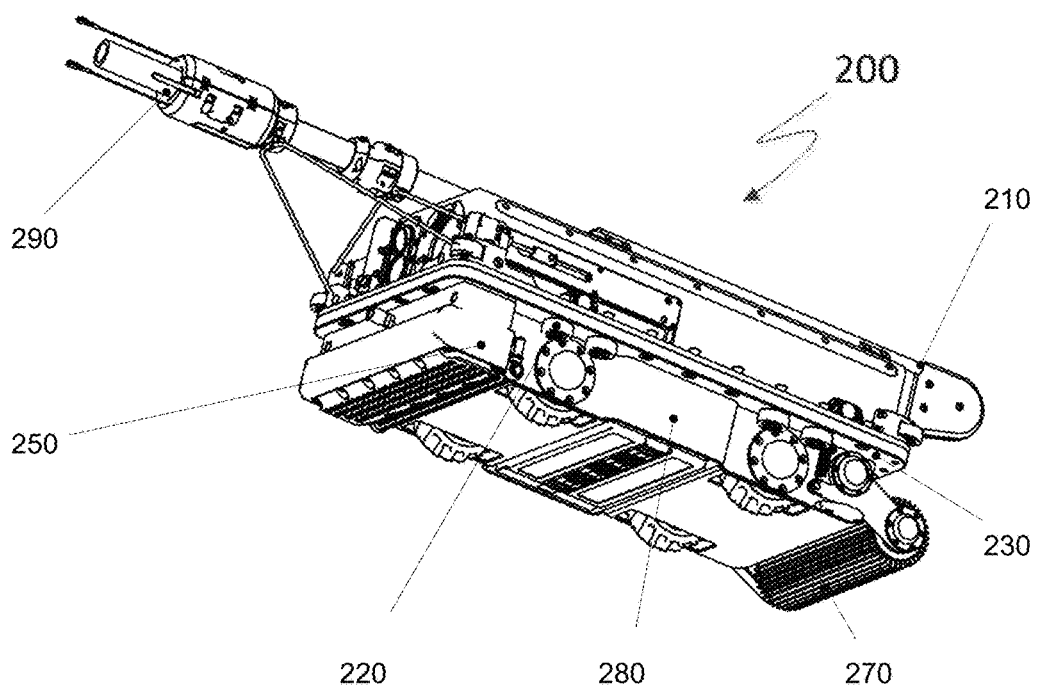
FIG. 4 shows a three-dimensional view of the apparatus for automated nondestructive inspection of a metal structure according to the second embodiment, providing visibility of the lower portion of said apparatus.

The apparatus for automated nondestructive inspection of a metal structure according to the second embodiment is shown in FIGS. 3 and 4, and it is a diagnostic automatic device 200 made in a form of four-wheel tractor 230 and with a sealed housing. The automatic device 200 is equipped with guides 210, rollers 220 for moving along the walls of the tank, located along the perimeter of the automatic device 200 housing on its side end, and a unit 270 for cleaning the surface of the metal structure to be inspected (for example, from impurities, sediment, crud, or deposits of various kinds). MFL unit 280 is arranged in the housing of the automatic device 200, and an ultrasound nondestructive inspection unit 250, having 96 channels, is mounted at the side ends of the housing of the automatic device 200. The automatic device 200 further comprises a sound imager 260, a front viewing camera 240, a pump 295 and an assembly joint 290 to enable the connection of the automatic device 200 with the means for delivery, a means for emergency retrieval and a communication line. The quantity and composition of elements of the apparatus can be changed when required; in particular, the nondestructive inspection unit can be added in the said housing in the other embodiments. The means for delivery of an automatic device 200 has the following dimensions and weight characteristics: size—1000×480×380 mm, weight—180 kg, minimum loading passage—510 mm.

The apparatus by the second embodiment in the form of an automatic device 200 is capable of measuring metal structures having thicknesses from 1.27 mm to 13.2 mm. The sealed housing of the automatic device 200 is made explosion-proof. Alternatively or in addition in other embodiments all parts of said apparatus including the nondestructive inspection units can be made explosion-proof. This enables the automatic device 200 to operate without the need of emptying and degassing of the tank, the bottom of which is inspected.

Between MFL unit 280 and the surface of the metal structure to be inspected there is a working gap, which can be changed by the automatic device 200. It is implemented by that in this embodiment the diagnostic automatic device 200 is equipped with a lifting mechanism for magnetic system of MFL unit 280, which allows it to change the working gap and pass over the obstacles while moving from plate to plate which are lap welded.

Figure 5:
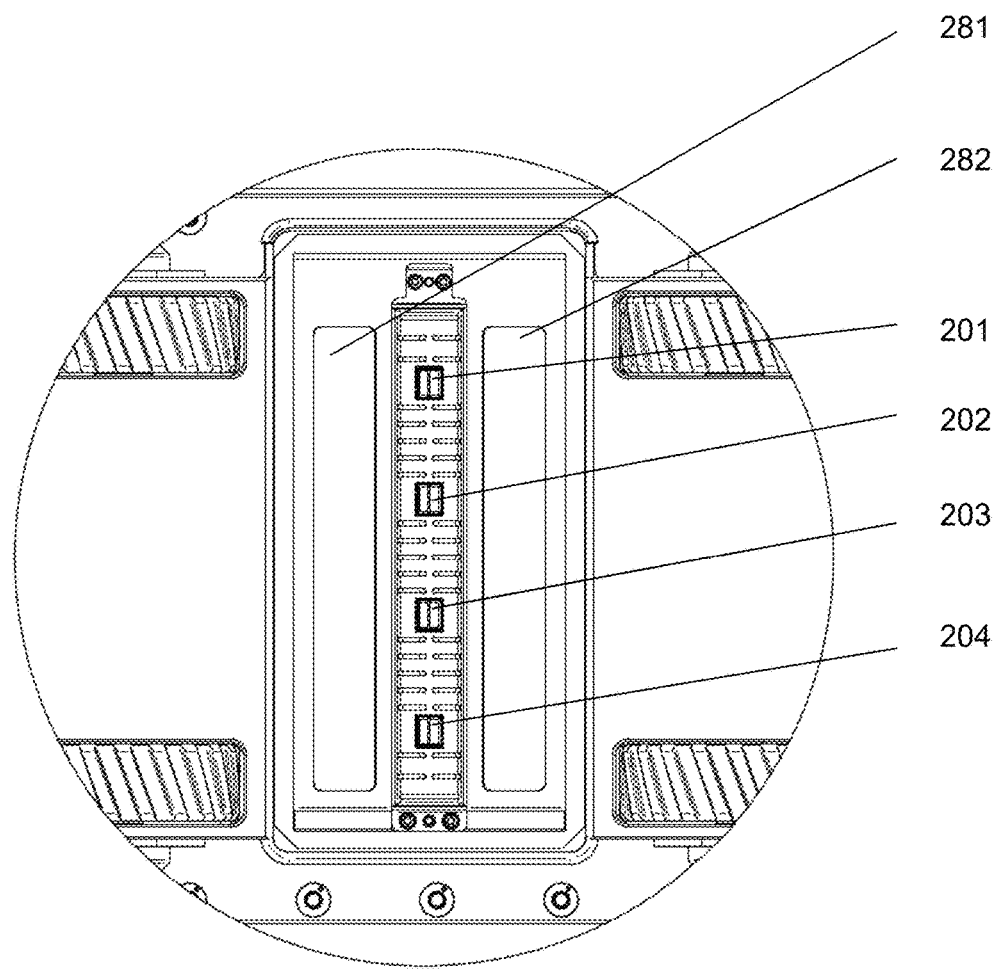
FIG. 5 shows position of eddy-current sensors of the eddy-current nondestructive inspection unit in relation to poles of the magnetic system of the unit for nondestructive inspection based on magnetic flux leakage method.

FIG. 5 illustrates position of eddy-current sensors 201, 202, 203, 204 of the eddy-current nondestructive inspection unit in relation to poles 281 and 282 of the magnetic system of the MFL unit 280.

Figure 6:
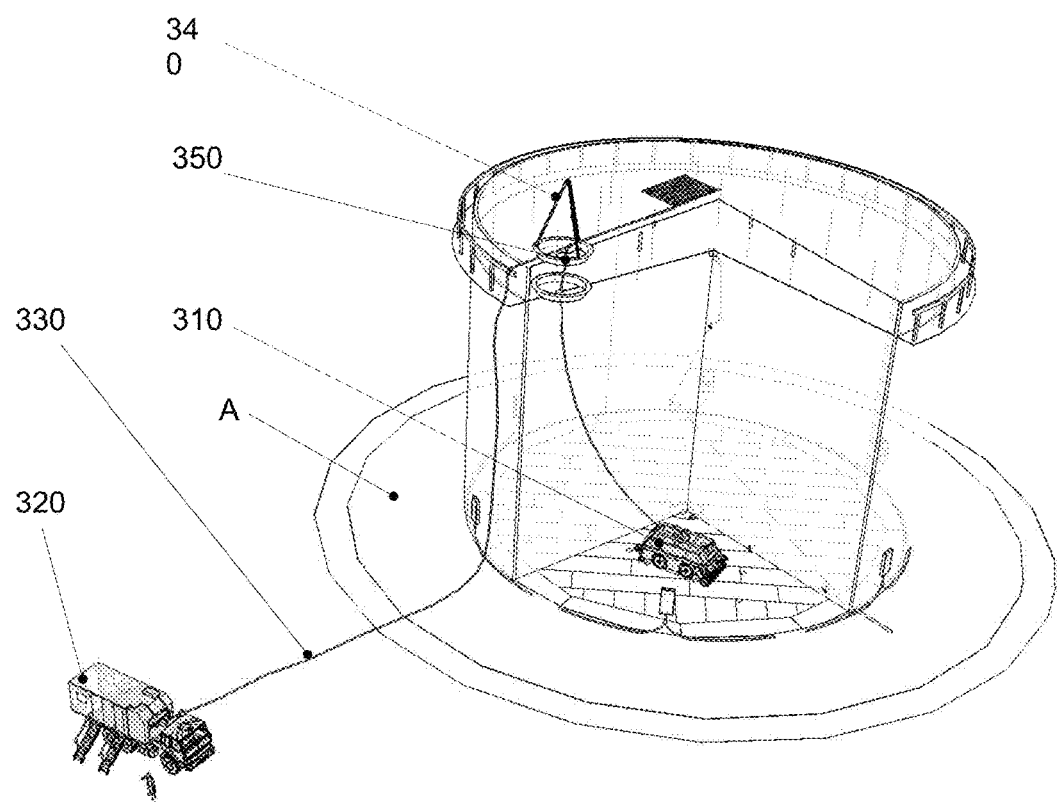
FIG. 6 shows the system for automated nondestructive inspection of a metal structure according to the present invention.

The apparatus according to the second embodiment in a form of an automatic device 200 also comprises a means for emergency removing said apparatus from a metal structure, for example, in the form of wires, as illustrated in FIG. 6.

The system for automated nondestructive inspection of a metal structure according to one of the embodiments of the present invention is shown in FIG. 6. This system can be used for inspection of petroleum storage tank floors and it comprises an apparatus 310 for automated nondestructive inspection of a metal structure according to one of the embodiments of the present invention and a control center in the form of a vehicle-mounted laboratory 320 intended to control the apparatus 310 and placed at some distance from a tank to be inspected (for example, 150 meters from explosive hazardous zone A, situated, for example, at a distance of 100 meters around the tank). The vehicle-mounted laboratory 320 is connected to the apparatus 310 via an explosion-proof communication line 330 to provide the ability to perform remote control of the apparatus 310 at a safe distance from the tank. The apparatus 310 is placed inside the tank through a manhole 350 arranged at the upper part of the tank by means of a loading system 340.

Figure 7:
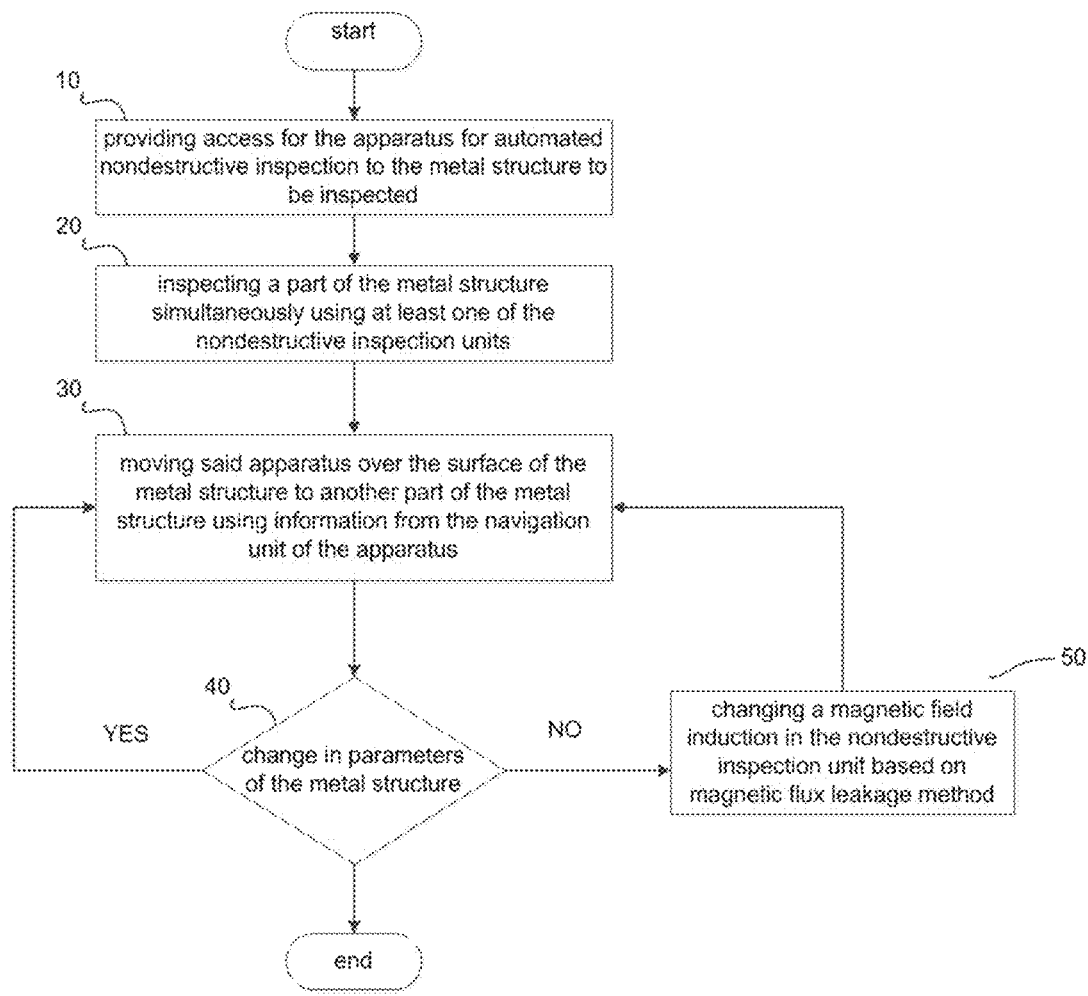
FIG. 7 shows the flowchart, illustrating a method for nondestructive inspection of a metal structure using the apparatus for automated nondestructive inspection of a metal structure according to the present invention.

During the automated nondestructive inspection of a metal structure performed by the apparatus for automated nondestructive inspection according to the present invention the method is applied, comprising steps illustrated in FIG. 7.

According to said method, first, said apparatus is placed so as to provide an access to the metal structure to be inspected, for example, at the bottom inside a storage tank for petroleum and petroleum products in order to detect defects at the bottom (step 10). It is important to note, that there is no need to empty and degas the tank, bottom of which is inspected.

Then, inspection of a metal structure part, for example, a tank bottom plate located close to said apparatus, is performed by one unit of, ultrasonic nondestructive inspection unit, MFL unit and eddy-current nondestructive inspection unit or more than one unit at the same time, if necessary (step 20).

Then, said apparatus is moved over the metal structure surface to another part of metal structure using information from an apparatus navigation unit (step 30).

In case of a change in parameters of metal structure, e.g., its thickness, at moving said apparatus through a butt or lap joint formed by metal plates or from plate to plate which are lap welded (step 40), the magnetic field induction in MFL unit is changed in such a way that apparatus could move through such portion of metal structure (step 50). In particular, to allow the movement of an apparatus above the butt or lap joint of a metal plate, the magnetic field induction in the MFL unit has to be reduced significantly or even reduced to zero, which may be achieved automatically or via a signal from the control center.

Furthermore, a working gap between the unit for nondestructive inspection based on the magnetic flux leakage method and a surface of the metal structure to be inspected can be further changed in the presence of obstacles on the metal structure surface in a form of contamination, sediment or deposits. Furthermore, contaminations, sediment or deposits may be cleaned by a unit for cleaning, available in said apparatus.

Therefore, inspection of a metal structure having variable thickness can be performed, for example, in the areas of butt or lap joints of plates, constituting such metal structure. Furthermore, when implementing this method, all units for nondestructive inspection can operate simultaneously complementing each other, thereby increasing the accuracy of metal structure inspection.

The present invention is not limited to the specific embodiments disclosed in the description for exemplary purposes, but covers all possible modifications and alternatives falling within the scope of the present invention specified by the claims.

What is claimed is:

1. An apparatus for automated nondestructive inspection of a metal structure having a surface, the apparatus comprising:
    an ultrasonic nondestructive inspection unit,
    a nondestructive inspection unit based on magnetic flux leakage method,
    an eddy-current nondestructive inspection unit,
    a control unit connected to the ultrasonic nondestructive inspection unit, the nondestructive inspection unit based on magnetic flux leakage method and the eddy-current nondestructive inspection unit for sending control signals to carry out inspection of the metal structure, and
    a navigation unit connected to the control unit, wherein the navigation unit determines a position of said apparatus relative to the metal structure, determines a state of the surface of the metal structure and sends signals into the control unit with information about the position of said apparatus and the state of the surface of the metal structure to be inspected,
    wherein all said units are installed in a housing,
    the control unit sends the control signals simultaneously to at least one of the ultrasonic nondestructive inspection unit, the nondestructive inspection unit based on the magnetic flux leakage method and the eddy-current nondestructive inspection unit based on the signals received from the navigation unit, and
    the nondestructive inspection unit based on the magnetic flux leakage method changes a magnetic field induction generated by this unit from a minimum value to a predetermined maximum value,
    the nondestructive inspection unit based on magnetic flux leakage method comprises an open magnetic system comprising at least two magnetic drums connected by a U-shaped flux guide frame and at least two pole pieces, wherein the at least two magnetic drums are positioned on parallel parts of the U-shaped flux guide frame,
    wherein said two magnetic drums are positioned at the at least two pole pieces, said two magnetic drums completely fill in cross-sections of the at least two pole pieces, said two magnetic drums are magnetized diametrically with a rotation axis directed along a magnetic pole of the magnetic system, and said two magnetic drums are configured to rotate with respect to each other, and
    said apparatus is used to inspect floors of storage tanks for petroleum, petroleum products, and petrochemicals.

2. The apparatus according to claim 1 further comprising at least one nondestructive inspection unit.

3. The apparatus according to claim 1, further comprising a unit for cleaning the surface of the metal structure.

4. The apparatus according to claim 1, wherein the nondestructive inspection unit based on magnetic flux leakage method is characterized by a working gap between this unit and the surface of the metal structure to be inspected and is configured to change said working gap.

5. The apparatus according to claim 1, further comprising a means of emergency removal of said apparatus from the metal structure.

6. The apparatus according to claim 1, wherein all said units are made explosion-proof and/or all said units are contained within sealed explosion-proof housings.

7. The apparatus according to claim 1, wherein the navigation unit comprises at least one sound imager, at least one ultrasound sensor and/or at least one camera.

8. The apparatus according to claim 1 used to inspect storage tanks for water.

9. A system for automated nondestructive inspection of a metal structure, the system comprising:
    the apparatus for automated nondestructive inspection of a metal structure according to claim 1, and
    a control center designed for controlling the apparatus and connected to the apparatus via an explosion-proof communication line.

10. The system according to claim 9, wherein the control center is a vehicle-mounted laboratory.

11. A method for nondestructive inspection of a metal structure by the apparatus according to claim 1, the method comprising:
    providing an access for said apparatus to the metal structure to be inspected,
    inspecting a part of the metal structure adjacent to said apparatus simultaneously using at least one of the ultrasonic nondestructive inspection unit, the nondestructive inspection unit based on magnetic flux leakage method and the eddy-current nondestructive inspection unit, and
    moving said apparatus over the surface of the metal structure to another part of the metal structure using information from the navigation unit of the apparatus,
    wherein a magnetic field induction in the nondestructive inspection unit based on magnetic flux leakage method is changed at a change in parameters of the metal structure.

12. The method as claimed in claim 11, wherein a working gap between the nondestructive inspection unit based on magnetic flux leakage method and the surface of the metal structure to be inspected is changed in case of presence of obstacles on the metal structure surface.

13. The method as claimed in claim 11, further comprising cleaning of the metal structure surface in case of detection of depositions present on the metal structure surface.

* * * * *